United States Patent
Uhland et al.

(10) Patent No.: US 8,882,748 B2
(45) Date of Patent: Nov. 11, 2014

(54) TRANSMUCOSAL DRUG DELIVERY DEVICE AND METHOD INCLUDING CHEMICAL PERMEATION ENHANCERS

(75) Inventors: Scott Uhland, San Jose, CA (US); Eric Peeters, Mountain View, CA (US); Hussain Fatakdawala, North Brunswick, NJ (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1195 days.

(21) Appl. No.: 12/576,087

(22) Filed: Oct. 8, 2009

(65) Prior Publication Data

US 2011/0087192 A1    Apr. 14, 2011

(51) Int. Cl.
*A61K 9/22* (2006.01)
*A61M 31/00* (2006.01)
*A61K 9/00* (2006.01)

(52) U.S. Cl.
CPC ............ *A61K 9/0036* (2013.01); *A61M 31/002* (2013.01)
USPC ...................... 604/890.1; 604/891.1; 604/514; 604/515

(58) Field of Classification Search
CPC .............. A61M 31/00; A61M 31/002; A61M 2210/1475; A61M 25/0041; A61M 2210/14
USPC .......... 604/890.1, 891.1, 48, 514, 515, 93.01, 604/285
See application file for complete search history.

(56) References Cited

U.S. PATENT DOCUMENTS

| | | | |
|---|---|---|---|
| 4,304,232 A | 12/1981 | Michaels | |
| 4,308,867 A | 1/1982 | Roseman et al. | |
| 4,402,695 A | 9/1983 | Wong | |
| 4,687,423 A | 8/1987 | Maget et al. | |
| 4,902,278 A | 2/1990 | Maget et al. | |
| 5,002,540 A | 3/1991 | Brodman et al. | |
| 5,062,834 A | 11/1991 | Gross et al. | |

(Continued)

FOREIGN PATENT DOCUMENTS

| | | |
|---|---|---|
| DE | 4130843 A1 | 3/1993 |
| WO | 94/01165 A1 | 1/1994 |

(Continued)

OTHER PUBLICATIONS

European Search Report for EP Application No. 10 18 7041 mailed Nov. 15, 2011.

(Continued)

*Primary Examiner* — Aarti B Berdichevsky
*Assistant Examiner* — Laura Schell
(74) *Attorney, Agent, or Firm* — Sutherland Asbill & Brennan LLP (57) ABSTRACT

Devices and methods are provided for transmucosal drug delivery. The transmucosal drug delivery device may include a housing configured for intralumenal deployment, such as intravaginally, into a human or animal subject; a drug-dispensing portion which contains at least one drug, the drug-dispensing portion being configured to dispense the drug from the housing by positive displacement; and a permeability enhancer-dispensing portion configured to release or generate a permeability enhancing substance to disrupt at least one region of a mucosal barrier adjacent to the housing at a selected time while intralumenally deployed in the human or animal subject. The device may be operable to dispense the drug from the housing to a region of the mucosal barrier disrupted by the permeability enhancing substance.

26 Claims, 3 Drawing Sheets

(56) References Cited

U.S. PATENT DOCUMENTS

| | | | |
|---|---|---|---|
| 5,090,963 A | 2/1992 | Gross et al. | |
| 5,112,614 A | 5/1992 | Magruder et al. | |
| 5,135,499 A | 8/1992 | Tafani et al. | |
| 5,318,557 A | 6/1994 | Gross | |
| 5,354,264 A | 10/1994 | Bae et al. | |
| 5,415,629 A | 5/1995 | Henley | |
| 5,522,804 A | 6/1996 | Lynn | |
| 5,593,552 A | 1/1997 | Joshi et al. | |
| 5,780,058 A | 7/1998 | Wong et al. | |
| 5,816,248 A | 10/1998 | Anderson et al. | |
| 5,928,195 A * | 7/1999 | Malamud et al. | 604/141 |
| 6,030,375 A | 2/2000 | Anderson et al. | |
| 6,086,909 A | 7/2000 | Harrison et al. | |
| 6,139,538 A | 10/2000 | Houghton et al. | |
| 6,183,434 B1 | 2/2001 | Eppstein | |
| 6,322,532 B1 | 11/2001 | D'Sa et al. | |
| 6,352,524 B1 | 3/2002 | Bunt et al. | |
| 6,423,039 B1 | 7/2002 | Rathbone et al. | |
| 6,444,224 B1 | 9/2002 | Rathbone et al. | |
| 6,450,991 B1 | 9/2002 | Bunt et al. | |
| 6,532,386 B2 | 3/2003 | Sun et al. | |
| 6,591,133 B1 | 7/2003 | Joshi | |
| 6,638,246 B1 | 10/2003 | Naimark et al. | |
| 6,756,053 B2 | 6/2004 | Zhang et al. | |
| 6,776,164 B2 | 8/2004 | Bunt et al. | |
| 6,805,877 B2 | 10/2004 | Massara et al. | |
| 6,835,392 B2 | 12/2004 | Hsu et al. | |
| 6,978,172 B2 | 12/2005 | Mori et al. | |
| 7,004,171 B2 | 2/2006 | Benita et al. | |
| 7,083,590 B1 | 8/2006 | Bunt et al. | |
| 7,486,989 B2 | 2/2009 | Sun et al. | |
| 7,497,855 B2 | 3/2009 | Ausiello et al. | |
| 7,732,408 B2 | 6/2010 | Josephson et al. | |
| 2002/0010414 A1 | 1/2002 | Coston et al. | |
| 2003/0018295 A1 | 1/2003 | Henley et al. | |
| 2003/0130558 A1 | 7/2003 | Massara et al. | |
| 2003/0219472 A1 | 11/2003 | Pauletti et al. | |
| 2004/0059388 A1* | 3/2004 | Herbst et al. | 607/2 |
| 2004/0082937 A1 | 4/2004 | Ausiello et al. | |
| 2004/0087893 A1 | 5/2004 | Kwon | |
| 2004/0219192 A1 | 11/2004 | Horstmann et al. | |
| 2005/0054969 A1* | 3/2005 | Hoff et al. | 604/20 |
| 2005/0124875 A1* | 6/2005 | Kawano et al. | 600/407 |
| 2005/0244502 A1 | 11/2005 | Mathias et al. | |
| 2005/0267440 A1 | 12/2005 | Herman et al. | |
| 2006/0024358 A1 | 2/2006 | Santini et al. | |
| 2006/0184092 A1 | 8/2006 | Atanasoska et al. | |
| 2007/0038181 A1 | 2/2007 | Melamud et al. | |
| 2007/0173711 A1* | 7/2007 | Shah et al. | 600/347 |
| 2007/0225634 A1* | 9/2007 | Ferren et al. | 604/27 |
| 2007/0269385 A1 | 11/2007 | Yun et al. | |
| 2008/0004564 A1* | 1/2008 | Smith | 604/20 |
| 2008/0004596 A1 | 1/2008 | Yun et al. | |
| 2008/0262412 A1 | 10/2008 | Atanasoska et al. | |
| 2008/0269666 A1 | 10/2008 | Wang et al. | |
| 2009/0131737 A1 | 5/2009 | Ferren et al. | |
| 2009/0171315 A1 | 7/2009 | Versi | |
| 2009/0306633 A1* | 12/2009 | Trovato et al. | 604/891.1 |

FOREIGN PATENT DOCUMENTS

| | | |
|---|---|---|
| WO | 94/18952 A1 | 9/1994 |
| WO | 97/41831 A1 | 11/1997 |
| WO | 01/12101 A1 | 2/2001 |
| WO | 2005/056708 A2 | 6/2005 |
| WO | 2005/089728 A2 | 9/2005 |
| WO | 2007/041119 A1 | 4/2007 |
| WO | 2007/047811 A2 | 4/2007 |
| WO | 2007/140416 A2 | 12/2007 |
| WO | 2009/081411 A2 | 7/2009 |

OTHER PUBLICATIONS

Hashimoto, et al. (2008). "Oxidative stress induces gastric epithelial permeability through claudin-3." Biochemical and Biophysical Research Communications. Retrieved from http://www.elsevier.com//locate/ybbrc. (5 pages).

Seth, et al. (Feb. 21, 2008). "Probiotics ameliorate the hydrogen peroxide-induced epithelial barrier disruption by a PKC- and MAP kinase-dependent mechanism." Am J Physiol Gastroentest Liver Physiol. Retrieved from http://www.ajpgi.org. (10 pages).

Bridges, et al., "Timed-Artificial Insemination in Beef Cows: What are the Options?," Purdue University Cooperative Extension Service, West Lafayette, IN (REV 3/08).

Sáfilho, O. G. et al., "Fixed-time artificial insemination with estradiol and progesterone for Bos indicus cows II: Strategies and factors affecting fertility," Science Direct, Theriogenology 72 (2009) 210-218.

* cited by examiner

TRANSMUCOSAL DRUG DELIVERY DEVICE AND METHOD INCLUDING CHEMICAL PERMEATION ENHANCERS

FIELD

The presently disclosed embodiments relate to implantable medical devices, and more particularly to devices and methods for the transmucosal delivery of drugs to a patient.

BACKGROUND

Transmucosal drug delivery is an area of interest because of the potential of delivering systemically-acting drugs with a high relative bioavailability by avoiding first-pass metabolism effects, the potential of locally delivering therapeutic agents to a site of interest, and the convenience of the application routes. Some of the possible sites for transmucosal drug delivery include the buccal, nasal, vaginal and rectal administration routes.

There are a number of challenges associated with transmucosal drug delivery, particularly with the transmucosal delivery of macromolecules comprising certain amino acid sequences. Enzymes present in fluid secreted by the mucosal tissue degrades certain amino acids. The types of enzymes exhibited by a mucosal tissue vary depending on the location of the mucosal tissue. Enzymes present in the vaginal fluid include nucleases, lysozyme, esterase, guaiacol peroxidase, aldolase, and β-glucuronidase. In addition, aminopeptidase, β-glucuronidase, phosphatases, lactate dehydrogenase, esterases, and type 5 phosphodiesterase are bound to the apical cell layers along the surface of the vaginal mucosa. The presence of these enzymes, particularly the aminopeptidases, is one factor that reduces the bioavailability of vaginally applied protein and peptide drugs.

Other mucosal tissues exhibit other enzymes which may degrade certain drugs. For example, the gastrointestinal tract exhibits mixed function oxidase systems, alcohol dehydrogenase, monoamine oxidase, reductases, p-nitroanisole demethylase, ethoxycournarin-o-deethylase, epoxide hydrolase, UDP-glucuronyltransferase, sulfokinase, glutathione-S-transferase, glycine transferase, acetyltransferase, and calechol-O-methyltransferase. These enzymes reduce the bioavailability of protein and peptide drugs applied to such mucosal tissues.

Furthermore, most mucosal tissues continuously excrete a viscous aqueous-based liquid. This viscous liquid presents additional challenges to transmucosal drug delivery. First, the viscous liquid traps and slows down the intrusion of foreign matter, thus allowing its intrinsic enzymatic and other defense mechanisms time to degrade and/or kill the foreign body. Secondly, the viscous liquid fluid continuously cleans and washes the surface of the mucosal tissue as it is expelled from the tissue. As such, a significant amount of drug may be wasted using conventional application techniques.

In the context of vaginal drug delivery, the vaginal mucosal membrane may be viewed as two barriers in series, an aqueous barrier and the mucosal membrane barrier. The mucosal lining is a stratified squamous epithelium that is glycogenated and nonkeratinized. The human vaginal epithelium consists of approximately 25 cell layers, depending on maturity and location. Like most other stratified epithelia, the human vaginal epithelium contains a tight junction (TJ) system, located in the uppermost cell layers. These TJs separate the apical cell surface domains from the basolateral cell surface domains and provide a primary barrier to the transmucosal delivery of water-soluble species. It is these epithelia and TJs present in all mucosa of the body, not just the vagina, that impede local administration of drug.

Accordingly, it would be desirable to provide devices and methods to improve the effectiveness of transmucosal drug delivery.

SUMMARY

In one aspect, an intralumenal device is provided for transmucosal drug delivery. The transmucosal drug delivery device may comprise a housing configured for intralumenal deployment into a human or animal subject; a drug-dispensing portion which contains at least one drug, the drug-dispensing portion being configured to dispense the drug from the housing by positive displacement; and a permeability enhancer-dispensing portion configured to release or generate a permeability enhancing substance to disrupt at least one region of a mucosal barrier adjacent to the housing at a selected time while intralumenally deployed in the human or animal subject. The device may be operable to dispense the drug from the housing to a region of the mucosal barrier disrupted by the permeability enhancing substance.

In another aspect, a method is provided for delivering a drug through a mucosal tissue from within a lumen. The method may include deploying a drug delivery device within the lumen; releasing from, or generating with, the device a permeability enhancing substance such that the permeability enhancing substance contacts a region of the mucosal tissue; and dispensing from the device a drug by a positive displacement process such that the drug is delivered to the region of the mucosal tissue that is contacted by the permeability enhancing substance.

In yet another aspect, an intravaginal device is provided for transmucosal drug delivery. The device may comprise a housing configured for intravaginal deployment into a human or animal subject; a drug dispenser containing a drug, the drug dispenser having one or more nozzles and a positive displacement element adapted to dispense the drug from the housing through the one or more nozzles by positive displacement; and a permeability enhancer dispenser configured to release or generate a permeability enhancing substance to disrupt at least one region of a mucosal barrier adjacent to the housing at a selected time while intravaginally deployed in the human or animal subject. The device may be operable to dispense the drug from the housing to a region of the mucosal barrier disrupted by the permeability enhancing substance.

DETAILED DESCRIPTION

A transmucosal drug delivery device is provided for intralumenal deployment. The term "intralumenal," as used herein, refers to placement within a body cavity, channel, tube, or the like, having a mucosal tissue wall. The term includes, but is not limited to, intravaginal, intrauterine, and intragastrointestinal tract (e.g., rectal) sites. The intralumenal deployment, or placement, of the device is generally maintained for the duration of delivery of at least one or more dosages of the drug. The deployed device may be retrieved from the lumen as desired, including for example, between delivery of individual dosages, following the delivery of several doses of drug, or following completion of a course of treatment of multiple doses. The device may be deployed until the drug payload is depleted.

In some embodiments, the transmucosal drug delivery device includes (i) a housing configured to allow deployment within a lumen, and (ii) one or more repositories for containing a drug and permeability enhancing substance. In certain embodiments, the drug and permeability enhancing substance are contained in separate repositories. The transmucosal drug delivery device may also comprise dispensing portions for dispensing the drug and permeability enhancing substance into the lumen or mucosal tissue wall. The drug delivery device may also include an integral control module for controlling the release or delivery of the drug and/or permeability enhancing substance from the device.

In another aspect, methods are provided for transmucosal drug delivery. The method includes placing, or deploying, the drug delivery device within the lumen of a patient, or a human or animal subject. The lumen may be, for example, a vagina, cervix, uterus, or part of the gastrointestinal tract, such as the rectum.

After the drug delivery device is placed in the lumen, the drug delivery device may actively generate or release the permeability enhancing substance onto the lumen or mucosal side wall. The drug delivery device may then dispense the drug to a region of the mucosal tissue disrupted by the permeability enhancing substance. The application of the permeability enhancing substance advantageously can enhance the drug transfer rate and/or amounts able pass undegraded through the mucosal barrier, thereby improving the effectiveness of the transmucosal administration of the drug.

The devices and methods described herein may further include one or more of the mucosal permeation enhancement features and techniques described in U.S. patent application Ser. No. 12/576,075 entitled "Transmucosal Drug Delivery Device and Method Including Microneedles" and in U.S. patent application Ser. No. 12/576,124 entitled "Transmucosal Drug Delivery Device and Method Including Electrically-Actuated Permeation Enhancement," which are filed concurrently herewith and which are incorporated by reference in their entirety.

Figure 1:
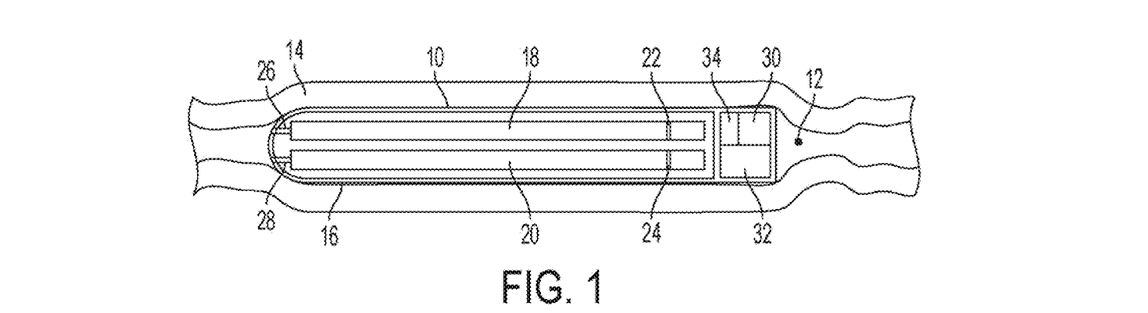
FIG. 1 is a section view, illustrating the placement of a transmucosal drug delivery device in a tissue lumen.

In some embodiments, a permeability enhancing substance and drug are contained in separate storage repositories in the device. For example, as illustrated in FIG. 1, a transmucosal drug delivery device 10 may be provided having a housing 16 comprising a permeability enhancer repository 18, a drug repository 20 and a control module 34. The housing 16 may be configured for placement within a lumen 12, having a mucosal tissue 14. The housing 16 includes a permeability enhancer dispenser for dispensing the permeability enhancing substance contained in the permeability enhancer repository 18 and a drug dispenser for dispensing the drug contained in the drug repository 20.

The permeability enhancer dispenser may include a nozzle 26 and actuator 22 that are together configured to dispense the permeability enhancing substance in an axial direction from the housing 16 (i.e., out of the end of the housing 16 into the lumen 12). The drug dispenser may also include a nozzle 28 and actuator 24 that are together configured to dispense the drug axially from the housing 16. Although the current example illustrates an axial dispensing arrangement, the device may also be configured to inject the permeability enhancing substance and the drug in a radial direction (i.e., out of the sidewall of the housing 16 in the direction of the mucosal tissue 14). For example, in alternate embodiments, the nozzles 26 and 28 may be positioned on one or more sides of the housing facing the mucosal tissue 14.

The control module 34 includes a power source 32, such as a battery, and controller 30. The controller 30 may be configured to control the timing and sequence of delivery of the drug and permeability enhancer, independently, by controlling actuator 22 and actuator 24. As is described in greater detail hereinafter, various actuator mechanisms may be used for actuators 22 and 24 to dispense the permeability enhancer and drug from the housing via a positive displacement process.

Figure 4:
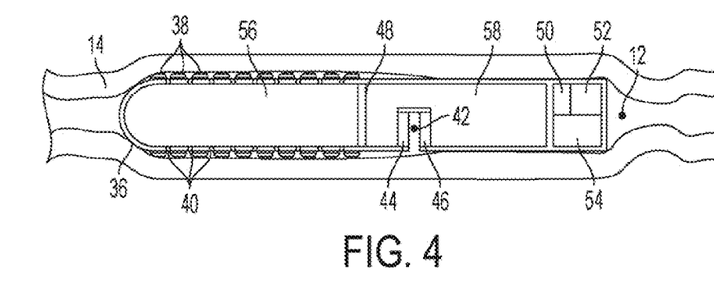
FIG. 4 is a section view, illustrating the placement of a transmucosal drug delivery device having permeation enhancer generation capabilities in a lumen.
Figure 5:
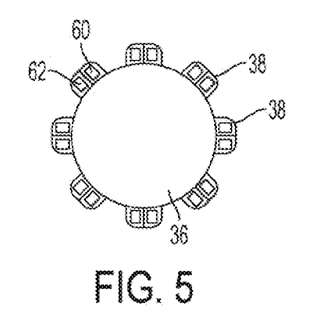
FIG. 5 is an end view, illustrating the transmucosal drug delivery device of FIG. 4.

In some embodiments, the permeability enhancing substance is generated outside of the housing and the drug is contained in a separate storage repository in the device. For example, as illustrated in FIG. 4, a transmucosal drug delivery device may be provided having a housing 36 containing a drug repository 56, a pump reservoir 58, and a control module 50. An array of electrochemical elements 38 is provided on the outside of housing 36 for generating a permeability enhancing substance at one or more periods while the housing 36 is deployed within a lumen 12. As illustrated in FIG. 5, the array of electrochemical elements 38 may be situated around the longitudinal sidewall of the housing 36. Alternatively, the array of electrochemical elements may be provided within the housing 36 for generating the permeability enhancing substance inside the housing 36. Each electrochemical element 38 may comprise a first pair of electrodes 60 and a second pair of electrodes 62. A mechanism for generating a permeability enhancing substance ($H_2O_2$) using the electrochemical elements 38 is described in greater detail below.

An array of dispensing nozzles 40 that are fluidly connected to the drug repository 56 may be provided on the side of housing 36 for delivering drug into the mucosal tissue 14. In other embodiments, one or more dispensing nozzles may be placed at the end of the housing 36 to dispense the drug in an axial direction. In such embodiments, one or more electrochemical elements may be placed at or proximal to the end of the housing 36 for generating the permeability enhancing substance near the site of drug delivery.

An internal gas-volume displacement pump may be provided in or adjacent to the pump reservoir 58 to actuate the dispensing of the drug contained in drug repository 56 via a positive displacement process. In one embodiment, the pump may include a cathode 44 and an anode 46 which contact water or an aqueous solution inside the pump reservoir 58. A channel 42 may be provided in housing 36 to allow aqueous secretions from the mucosal tissue 14 to enter the channel 42 and contact the cathode 44 and anode 46. In other embodiments, a channel 42 that is in fluid communication with the interior space of the lumen may be omitted and electrolytes may be provided on board the device. For example, the pump reservoir 58 may comprise an ionic solution such as sodium nitrite. Alternatively, the pump reservoir 58 may contain deionized water, and a solid electrolyte may be provided in place of the channel 42 so that the solid electrolyte contacts the surfaces of the cathode 44 and anode 46 facing the channel 42. A mechanism for generating a gas inside the pump reservoir 58 using the cathode 44 and anode 46 is described in greater detail hereinafter.

The control module 50 includes a power source 54, such as a battery, and controller 52. The controller 52 may be configured to control the timing and sequence of delivery of the drug and permeability enhancer, independently, by applying electrical potentials to the electrochemical elements 38 and the cathode 44 and anode 46. As is described in greater detail below, various other actuator mechanisms may be used to dispense the drug from the housing via a positive displacement process.

A. Housing

The housing is generally configured to facilitate deployment of the drug delivery device within a mucosal lumen. In some embodiments, the device may be placed within the lumen by insertion into the lumen via an exterior body orifice. Accordingly, in some embodiments, the housing is shaped and dimensioned to allow insertion and placement, i.e., deployment, of the device within the intended lumen via the exterior body orifice. Specifically, the housing may be shaped and dimensioned for vaginal, cervical, uterine, or rectal insertion and placement. The materials of construction, size, shape, and surface features and other characteristics of the device housing are configured so that the device can be deployed into the mucosal lumen, retained securely in the lumen during operation of the device, and generally retrieved from the lumen following operation of the device or when otherwise desired to be removed. The device configuration is based upon the particular lumenal site and human or animal anatomical considerations, for deployment with minimal discomfort to the patient.

The housing may include one or more repositories disposed therewithin for containing drugs and/or permeability enhancing substances. The housing may also contain dispensers for dispensing the drug and/or permeability enhancing substance and a control module for controlling the release and delivery of the drug and/or permeability enhancing substance. The dispensers may include nozzles for dispensing the drug and/or permeability enhancing substances therethrough. These nozzles may be arranged to inject the drug and/or permeability enhancing substance in an axial direction relative to the housing (i.e., out of an end of the housing), in a radial direction relative to the housing (i.e., out of a sidewall of the housing), or in a combination thereof. The drug and permeability enhancing substances may be contained in separate housings. Separate storage may advantageously facilitate ease of formulating the drug, as certain co-formulations may present difficulties with compatibility and/or solvent selection.

The housing may be formed of any biocompatible material. Moreover, the housing material may be resistant to degradation in the environment of the lumen. Examples of suitable materials include stainless steel, titanium, and certain polymers. The material forming the housing may include a coating to enhance biocompatibility and/or operation of the device.

B. Drug Dispenser

A drug dispenser is provided for actively dispensing the drug from the drug delivery device by positive displacement. The drug may be stored in the device in a repository and dispensed through one or more nozzles into the lumen or mucosal tissue at selected times. The drug dispenser may be arranged to dispense the drug from the housing to a region of the mucosal barrier disrupted by the permeability enhancing substance.

The drug dispenser may employ various positive displacement elements for dispensing the drug from the device including mechanical displacement, osmotic swelling displacement, gas-volume displacement, electrostatically-induced compression, piezoelectric actuation, or a thermally/magnetically induced phase transformation. The positive displacement element may comprise an actuatable dispensing valve in combination with a static pressure head. The term "positive displacement," as used herein, generally refers to any process whereby the drug is dispensed from the drug delivery device under force provided from within the drug delivery device. Accordingly, the term does not refer to the passive, chemical diffusion of the drug out of the device.

In some embodiments, the drug is stored within a repository within the housing, and is actively dispensed from the housing through one or more dispensing nozzles by a mechanical displacement element such as a piston or spring. For example, in the embodiment of FIG. 1, the integral control module 34 may selectively transmit electrical or mechanical power to the actuator 22, advancing the piston of the actuator 22 through the drug repository 20 and dispensing the drug through the dispensing nozzle 28.

In some embodiments, the drug is dispensed by gas-volume displacement. For example, as illustrated in FIG. 4, the device may include a pump reservoir 58 containing water or an aqueous solution. A pair of electrodes (a cathode 44 and an anode 46) may be provided within the pump reservoir 58 for generating a gas, such as oxygen. A passage 42 is provided between the electrodes to allow water from within the lumen 12 to exchange protons and electrons with the water or aqueous solution within the pump reservoir 58. In other embodiments, a channel 42 that is in fluid communication with the interior space of the lumen may be omitted and electrolytes may be provided on board the device. For example, the pump reservoir 58 may comprise an ionic solution such as sodium nitrite. Alternatively, the pump reservoir 58 may contain deionized water, and a solid electrolyte may be provided in place of the channel 42 so that the solid electrolyte contacts the surfaces of the cathode 44 and anode 46 facing the channel 42.

An electrical potential of about 1.0 V or greater may be applied to the electrodes to generate $O_2$ at the anode. The reaction at the anode is described by EQ. 1. In the water, at the negatively charged cathode, a reduction reaction takes place, with electrons from the cathode being given to the hydrogen cations to form hydrogen gas as shown in EQ. 2. The pressure exerted by the generated oxygen and hydrogen causes piston 48 to advance into the drug repository 56, thereby causing the drug to dispense through the dispensing nozzles 40 into the lumen 12 or the mucosal tissue 14. The production of oxygen and hydrogen may be controlled by an integral control module 50 that is provided on-board the device in the housing 36. The control module 50 may include a power source 54, such as a battery, and a controller 52 that is programmed to supply the electrical potential to the cathode 44 and the anode 46 at a selected time.

$$2H_2O(l) \rightarrow O_2(g) + 4H^+(aq) + 4e^- \qquad \text{EQ. 1}$$

$$2H^+(aq) + 2e^- \rightarrow H_2(g) \qquad \text{EQ. 2}$$

Figure 7:
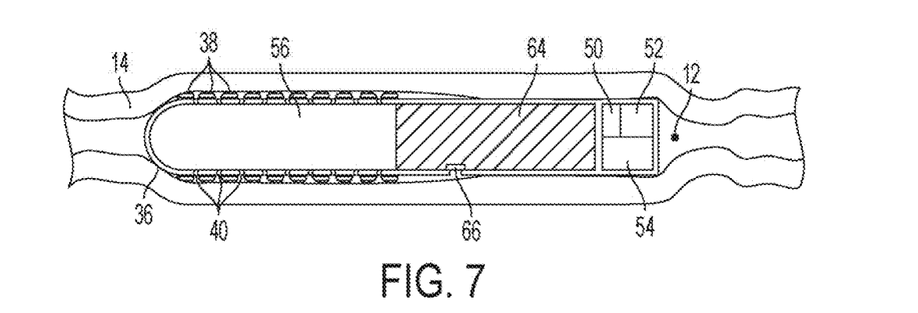
FIG. 7 is a section view, illustrating an alternate embodiment of a transmucosal drug delivery device.
Figure 8:
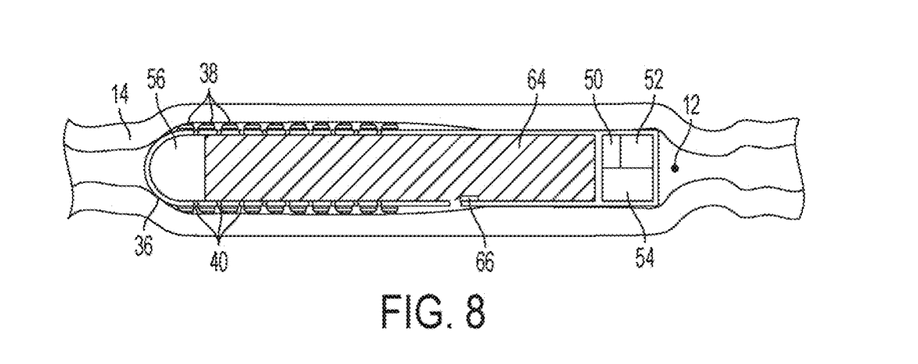
FIG. 8 is a section view, illustrating the delivery of a drug from the transmucosal drug delivery device of FIG. 7.

Other positive displacement elements may be better understood with reference to FIGS. 7 and 8. In these examples, a drug contained in a drug repository 56 is dispensed by the enlargement of component 64. Component 64 may be, for example, a swellable material (such as a swellable gel) or an enlargeable repository. In some embodiments, the drug is dispensed by osmotic swelling displacement. Optionally, a valve 66 may be provided to selectively control the ingress of water into the repository or swellable material. Water from the lumen 12 may be drawn into a repository or swellable material, causing the repository or swellable material to expand in volume. The expansion of the repository or swellable material may displace a volume of drug contained within the housing, causing the drug to be dispensed from the device into the lumen. The actuation of the valve 66 may be controlled by the integral control module 50.

In other embodiments, the drug may be dispensed by an expansive force supplied by an induced phase transformation. For example, component 64 may comprise an expandable reservoir containing a phase-transformable material. The phase-transformable material may be any liquid or solid that will undergo a phase transition from solid or liquid to gas when heated or subjected to an electro-magnetic field. When the material transforms to a gas, the material expands and advances through the drug repository 56 to dispense the drug from the device. The actuation of the phase-transformation may be controlled by the on-board control module 50.

In other embodiments, the drug may be positively displaced and dispensed from the housing by electrostatically-induced compression or using a piezoelectric actuator. For example, a dielectric elastomeric actuator or piezoelectric actuator may be arranged such that a change in voltage or current to the actuator causes the actuator to exert a compressive force on the drug in the drug repository. This compressive force may cause the drug to be dispensed from the device. The actuation of the actuator may be controlled by the on-board control module.

In other embodiments, positive displacement of the drug may be achieved using a static pressure head and an actuatable valve. The valve may be operated, for example, in an analog mode for amplitude-modulated dosing or it may be operated in a digital mode for frequency/duty-cycle modulated dosing. The static head pressure may be provided by loading the drug into the device under pressure or the device may be pressurized after the drug is loaded in the device.

Drugs

Various drugs may be administered from the drug delivery device. The drug may be a protein or a peptide. For example, in some embodiments, the drug delivery device may be used to administer hormones or steroids, including, but not limited to, follicle stimulating hormone, parathyroid hormone, luteinizing hormone, gonadotropin-releasing hormone (GnRH), estradiol, progesterone, melatonin, serotonin, thyroxine, triiodothyronine, epinephrine, norepinephrine, dopamine, antimullerian hormone, adiponectin, adrenocorticotropic hormone, angiotensinogen, angiotensin, antidiuretic hormone, atrial-natriuretic peptide, calcitonin, cholecystokinin, corticotropin-releasing hormone, erythropoietin, gastrin, ghrelin, glucagon, growth hormone-releasing hormone, human chorionic gonadotropin, human placental lactogen, growth hormone, inhibin, insulin, insulin-like growth factor, leptin, melanocyte stimulating hormone, orexin, oxytocin, prolactin, relaxin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estrone, estriol, calcitriol, calcidiol, prostaglandins, leukotrienes, prostacyclin, thromboxane, prolactin releasing hormone, lipotropin, brain natriuretic peptide, neuropeptide Y, histamine, endothelin, enkephalin, renin, and pancreatic polypeptide.

In some embodiments, the drug delivery device may be used to administer cytokine signaling molecules or immunomodulating agents that are used in cellular communication. These molecules commonly comprise proteins, peptides, or glycoproteins. Cytokine signaling molecules include, for example, the four α-helix bundle family which include the IL-2 subfamily (e.g., erythropoietin (EPO) and thrombopoietin (THPO)), the interferon (IFN) subfamily and the IL-10 subfamily. Cytokine signaling molecules also include the IL-1, IL-18, and IL-17 families.

In some embodiments, the drug delivery device may be used to administer drugs for pain management, including, but not limited to, corticosteroids, opioids, antidepressants, anticonvulsants (antiseizure medications), non-steroidal anti-inflammatory drugs, COX2 inhibitors (e.g., rofecoxib and celecoxib), ticyclic antidepressants (e.g., amitriptyline), carbamazepine, gabapentin and pregabalin, codeine, oxycodone, hydrocodone, diamorphine, and pethidine.

In some embodiments, the drug delivery device may be used to administer cardiovascular drugs. Examples of cardiovascular drugs that may be administered with the device include B-type natriuretic peptide (BNP), atrial natriuretic peptide (ANP), atrial natriuretic factor (ANF), atrial natriuretic hormone (ANH), and atriopeptin. Cardiovascular drugs that may be administered by the device also include, for example, antiarrhythmic agents, such as Type I (sodium channel blockers), including quinidine, lidocaine, phenytoin, propafenone; Type II (beta blockers), including metoprolol; Type III (potassium channel blockers), including amiodarone, dofetilide, sotalol; Type IV (slow calcium channel blockers), including diltiazem, verapamil; Type V (cardiac glycosides), including adenosine and digoxin. Other cardiacvascular drugs that may be administered by the device include ACE inhibitors, such as, for example, captopril, enalapril, perindopril, ramipril; angiotensin II receptor antagonists, such as, for example, candesartan, eprosartan, irbesartan, losartan, telmisartan, valsartan; beta blocker; and calcium channel blocker.

The drug may be formulated with one or more pharmaceutically acceptable excipients as needed to facilitate the drug's storage in and release from the device. In one embodiment, the drug may be in a liquid solution or suspension. The drug may be in the form of microparticles or nanoparticles. The solvent or carrier may be aqueous or organic.

C. Permeability Enhancer Dispenser

A permeability enhancer dispenser may be provided for dispensing a permeability enhancing substance from the housing. The permeability enhancing substance may be stored in the device or it may be generated by the device. As used herein, the terms "dispenser" and "dispensing portion," when referring to the permeability enhancer or permeability enhancing substance, mean the portion or features of the device that release, generate, or release and generate the permeability enhancer or permeability enhancing substance.

In one embodiment, the permeability enhancing substance is stored in a repository and then dispensed from the device via diffusion or an active process, such as a positive displacement process. Any of the previously described examples of positive displacement mechanisms, including, but not limited to, mechanical displacement, osmotic swelling displacement, gas-volume displacement, electrostatically-induced compression, piezoelectric actuation, a thermally/magnetically induced phase transformation, or an actuatable dispensing valve in combination with a static pressure head may also be used for dispensing a permeability enhancing substance from a repository.

In some embodiments, the permeability enhancing substance is generated by the device inside or outside of the housing. In certain embodiments, the permeability enhancing substance is generated in vivo. For example, the housing may comprise an external dispenser for generating and dispensing hydrogen peroxide ($H_2O_2$) into the mucosal tissue. The generation of hydrogen peroxide may be accomplished using water, electricity and oxygen. The water may be provided in the device or may be obtained from the environment within the lumen. Electricity may be provided by an on-board power source. Oxygen may be provided for the reaction by dissolving oxygen in a fluid contained in the device, by trapping or supplying air to the device, or by electrochemical generation.

As illustrated in FIG. 4, an array of electrochemical elements 38 may be provided on the exterior of the housing 36. Each of the electrochemical elements 38 may comprise a two sets of isolated electrodes and proton exchange membranes. A first pair of electrodes may be arranged such that the anode extends away from the housing 36 into the lumen 12. An electrical potential of about 1.0 V or greater may be applied to this electrode to generate $O_2$ at the anode from water present in the lumen 12. The reaction at the anode is described by EQ. 1. A second pair of electrodes, which may be adjacent to the first pair of electrodes may be arranged such that the cathode extends away from the housing 36 into the lumen 12. An electrical potential of about 1.6 V to about 2.0 V may be applied to this electrode to generate $H_2O_2$ at the cathode. The reaction at the cathode is described by EQ. 3.

$$O_2 + 2H^+(aq) + 2e^- \rightarrow H_2O_2(aq) \quad\quad \text{EQ. 3}$$

The production of $H_2O_2$ may be controlled by an integral control module 50 that is provided on-board the device in the housing 36. The control module 50 may include a power source 54, such as a battery, and a controller 52 that is programmed to activate the electrochemical elements 38 at a one or more selected times.

Permeability Enhancers

Various permeability enhancing substances may be provided. The term "permeability enhancing substance" refers to substances that facilitate the delivery of a drug across the mucosal tissue. The term encompasses chemical enhancers that, when applied to the mucosal tissue, render the tissue more permeable to the drug and enzyme inhibitors that prevent degradation of the drug by mucosal tissue enzymes. Chemical enhancers include such substances as dimethyl sulfoxide (DMSO), hydrogen peroxide ($H_2O_2$), propylene glycol, oleic acid, cetyl alcohol, benzalkonium chloride, sodium lauryl sulphate, isopropyl myristate, Tween 80, dimethyl sulfoxide, dimethyl formamide, dimethyl acetamide, sodium lauroylsarcosinate, sorbitan monolaurate, methylsulfonylmethane, Azone, terpenes, phosphatidylcholine dependent phospholipase C, triacyl glycerol hydrolase, acid phosphatase, phospholipase A2, and concentrated saline solutions (e.g., PBS and NaCl).

Enzyme inhibitors include reversible inhibitors and irreversible inhibitors. Reversible inhibitors include, for example, protease inhibitors and antiretrovirals, such as saquinavir, ritonavir, indinavir, nelfinavir, amprenavir, lopinavir, atazanavir, fosamprenavir, tipranavir and darunavir. Irreversible inhibitors include, for example, diisopropylfluorophosphate (DFP), α-difluoromethylornithine (DFMO), trypanothione reductase, methotrexate, allopurinol, and acyclovir.

D. Control Module

A control module is provided for controlling the delivery of the permeability enhancing substance and drug into the mucosal tissue. The control module may be provided on-board the drug delivery device in the housing. The control module may include a power source and a controller. The power source may be any source of mechanical or electrical power, such as a battery or fuel cell. The controller may be programmable or it may be pre-programmed to deliver the permeability enhancing substance and drug in accordance with a pre-designated schedule.

In some embodiments, the control module may further comprise one or more sensors for analyzing the environment around the device or within the lumen. For example, a sensor may be employed to detect the presence of a drug-degrading enzyme in the lumen. In such embodiments, the controller may be further configured to dispense the drug after the abatement of the drug-degrading enzyme is detected or other suitable environmental conditions are detected for drug delivery.

In some embodiments, the control module may further comprise a wireless receiver for receiving wireless control signals from a separate, detached transmitting device. In certain embodiments, the device may be deployed into the lumen by the patient or a physician, and, thereafter, the patient or physician may actuate the release of the permeability enhancer and drug using the transmitting device to transmit control signals to the placed device. Furthermore, in some embodiments, the control module receiver and transmitting device may both be transceivers capable of transmitting and receiving control signals and other communications from each other. Accordingly, in certain embodiments, the control module transceiver may transmit data relevant to the operation of the device, such as data regarding the dosages already administered, the dosing schedule, the level of drug or permeation enhancing substance remaining in the repositories, and the remaining battery charge, as well as data relevant to the environment of the lumen, such as data detected or measured by an integral sensor. In some embodiments, the control module may also be wirelessly powered.

In various embodiments, the device may be configured for wireless operation, e.g., following deployment in the human or animal subject. In such cases, the device includes appropriate telemetry components as known in the art. For example, actuation of the dispensing and/or generation of the permeation enhancing substance and/or the drug dispensing may be done from a remote controller, e.g., external to the human or animal subject. Generally, the telemetry (i.e. the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry systems known in the art also may be used. In another case, the device is configured to be remotely powered, or charged. For example, the device may include a transducer for receiving energy wirelessly transmitted to the device, circuitry for directing or converting the received power into a form that can be used or stored, and if stored, a storage device, such as a rechargeable battery or capacitor. In still another case, the device is both wirelessly powered and wirelessly controlled.

E. Methods

Methods are provided for transmucosal drug delivery using intralumenal devices. The method includes placing the drug delivery device within the lumen of a patient. The patient may be a human or other mammalian animal (e.g., cow, horse, pig, or dog). The methods include various medical and veterinary therapies, as well as animal husbandry applications. The lumen may be, for example, a vagina, cervix, uterus, bladder, or rectum. The device may be adapted to contact essentially any mucosal tissue surface. The device may be placed in the lumen by inserting the device through an exterior orifice of the patient into the lumen. In some embodiments, the device may be in a form that may be orally administered for delivery of a drug via the mucosal tissue of the gastrointestinal tract.

After the drug delivery device is placed in the mucosal lumen, the drug delivery device may actively generate or release the permeability enhancing substance directly into the lumen or mucosal side wall. The generation or release of the permeability enhancing substance may be actuated by an integral control module at a selected time. The drug delivery device may then dispense the drug to a region of the mucosal tissue disrupted by the permeability enhancing substance. This method and sequence of administration may advantageously reduce or avoid degradation of the drug, particularly a protein drug, that might otherwise occur at the mucosal surface without the permeation enhancement. The release of the drug from the device may also be actuated by the control module at another selected time after the permeability enhancing substance has been released or has disrupted the mucosal tissue.

Figure 2:
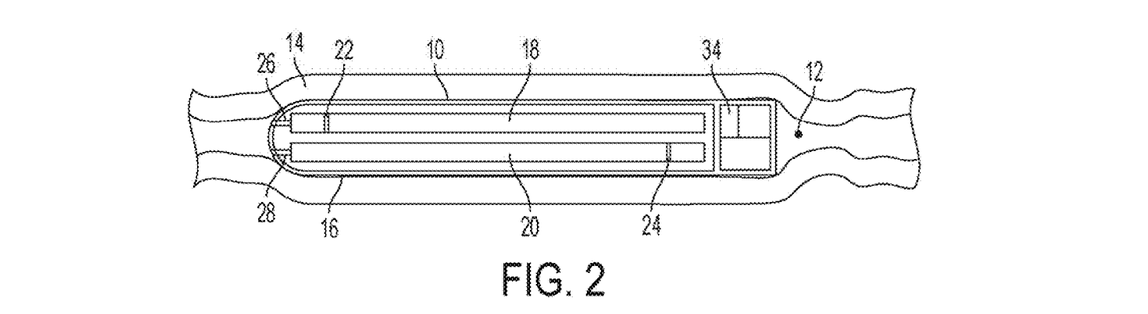
FIG. 2 is a section view, illustrating the delivery of an permeability enhancing substance from a drug delivery device placed within a lumen.
Figure 3:
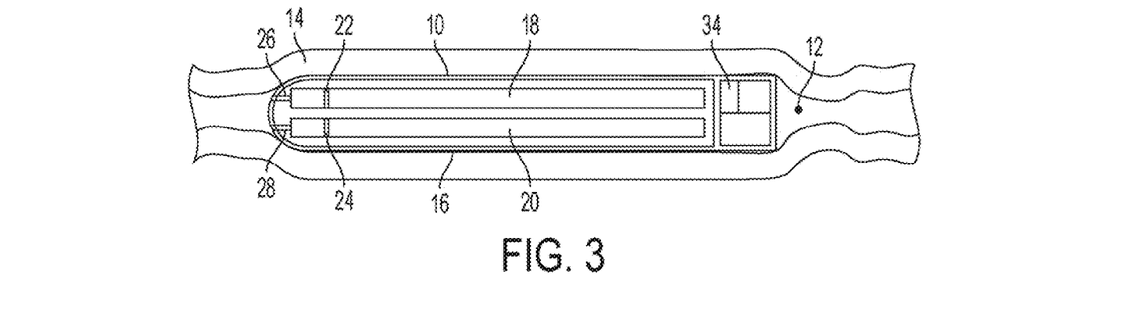
FIG. 3 is a section view, illustrating the delivery of a drug from a drug delivery device placed within a lumen after delivery of the permeability enhancing substance.

As illustrated in FIG. 1, the transmucosal drug delivery device 10 may be placed in a lumen 12. The drug delivery device 10 may be held in place by frictional engagement between the mucosal tissue 14 and the housing 16. As illustrated in FIG. 2, a permeability enhancing substance may then be dispensed from the repository 18 through the nozzle 26 via actuation of the actuator 22. The actuation of the actuator 22 may be controlled by the control module 34. As illustrated in FIG. 3, after the permeation enhancer has disrupted the mucosal tissue by inhibiting enzyme activity or rendering the mucosal tissue 14 more permeable to the drug, the drug is dispensed from the repository 20 through the nozzle 28 via actuation of the actuator 24. The actuation of the actuator 24 may also be controlled by the control module 34. The device may thereafter be removed from the lumen.

Figure 6:
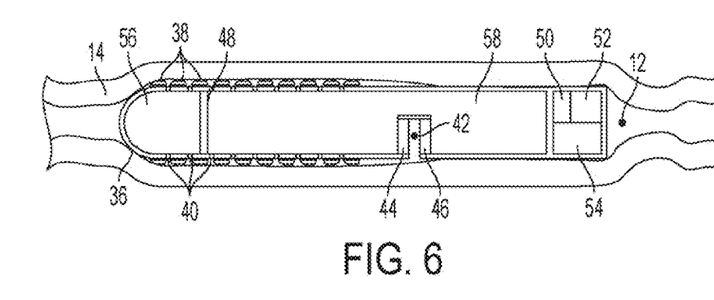
FIG. 6 is a section view, illustrating the delivery of drug from the device of FIG. 4 after generation of the permeation enhancer.

With reference to FIG. 4, in embodiments in which the permeation enhancing substance is generated by the device, the control module 50 may first actuate the array of electrochemical elements 38 to generate the permeation enhancing substance. After the permeation enhancing substance is generated, the control module 50 may actuate the delivery of the drug by applying an electrical potential to the cathode 44 and the anode 46. As illustrated in FIG. 6, as gas is generated within the pump reservoir 58, the piston 48 advances through the drug repository 56, causing the drug to be dispensed through the nozzles 40. The device may thereafter be removed from the lumen.

With reference to FIG. 7, in embodiments in which a swellable material or enlargeable repository is used, the permeation enhancer is first generated or dispensed from the device. For example, the control module 50 may apply an electrical potential to each of the electrochemical elements 38 to generate the permeation enhancing substance. The valve 66 may then be actuated to allow the ingress of water into the swellable material or expandable reservoir 64. Alternatively, the control module 50 may actuate the inducement of a phase change of a material in the expandable reservoir 64. For example, the control module 50 may actuate a heating element to heat the phase change material or may actuate a circuit that generates an electro-magnetic field. As illustrated in FIG. 8, the enlargement of the swellable material or expandable reservoir 64 forces the drug out of the nozzles 40 and into the mucosal tissue 14.

Applications/Uses

The drug delivery device and method may be used for various medical and therapeutic applications. In some embodiments, the drug delivery device may be used to treat infertility in a female subject. For example, the drug delivery device may be placed in the vagina (or uterus, or other part of the birth canal) of a female subject. The drug delivery device may then dispense and/or generate a permeability enhancing substance into the lumen. Thereafter, the drug delivery device may deliver follicle stimulating hormone to induce ovulation in the female subject. In some embodiments, the drug delivery device may be configured to deliver a plurality of hormones, including follicle stimulating hormone, luteinizing hormone, gonadotropin-releasing hormone separately, or in combination, in appropriate sequences, at appropriate times, and in appropriate amounts to treat infertility. The device may also dispense estradiol to regulate natural hormone production in the female subject. The appropriate dosing schedule and amounts may be determined by one in the field of reproductive pharmacology.

In another embodiment, the drug delivery device may be use to treat insulin dependent diabetes (Type I diabetes) in a subject. The drug delivery device may be placed within a lumen of the subject. The drug delivery device may then dispense and/or generate a permeability enhancing substance into the lumen. Thereafter, the drug delivery device may deliver insulin (Humulin R, Novolin R), insulin isophane (Humulin N, Novolin N), insulin lispro (Humalog), insulin aspart (NovoLog), insulin glargine (Lantus) or insulin detemir (Levemir) to the patient at a selected time or times.

In another embodiment, the drug delivery device may be use to treat diabetes mellitus (Type II diabetes) in a subject. The drug delivery device may be placed within a lumen of the subject. The drug delivery device may then dispense and/or generate a permeability enhancing substance into the lumen. Thereafter, the drug delivery device may deliver exenatide to the patient at a selected time or times.

In another embodiment, the drug delivery device may be use to treat breast or ovarian cancer in a subject. The drug delivery device may be placed within a lumen of the subject, such as the vagina for a female subject. The drug delivery device may then dispense and/or generate a permeability enhancing substance into the lumen. Thereafter, the drug delivery device may deliver abraxane (or other drug effective in the treatment or management of cancer) to the patient at a selected time or times.

In another embodiment, the drug delivery device may be use to treat HIV/AIDS in a subject. The drug delivery device may be placed within a lumen of the subject. The drug delivery device may then dispense and/or generate a permeability enhancing substance into the lumen. Thereafter, the drug delivery device may deliver Abacavir (ABC) or Cidofovir (or other drug effective in the treatment or management of HIV/AIDS) to the patient at a selected time or times. The device also may be used to treat other sexually transmitted diseases.

In another embodiment, the drug delivery device may be use to treat genital herpes in a subject. The drug delivery device may be placed within a lumen of the subject, such as within the vagina of a female subject. The drug delivery device may then dispense and/or generate a permeability enhancing substance into the lumen. Thereafter, the drug delivery device may deliver acyclovir, famciclovir, or valacyclovir (or other drug effective in the treatment or management of genital herpes) to the patient at a selected time or times.

In another embodiment, the drug delivery device may be use to treat diabetes insipidus in a subject. The drug delivery device may be placed within a lumen of the subject. The drug delivery device may then dispense and/or generate a permeability enhancing substance into the lumen. Thereafter, the drug delivery device may deliver desmopressin (or other drug effective in the treatment or management of diabetes insipidus) to the patient at a selected time or times.

In another embodiment, the drug delivery device may be use to treat osteoporosis in a subject. The drug delivery device may be placed within a lumen of the subject, such as within the vagina of a female subject. The drug delivery device may then dispense and/or generate a permeability enhancing substance into the lumen. Thereafter, the drug delivery device may deliver ibandronate, calcitonin, or parathyroid hormone (or other drug effective in the treatment or management of osteoporosis) to the patient at a selected time or times.

It will be appreciated that various of the above-disclosed and other feature and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

We claim:

1. An intravaginal device for transmucosal drug delivery comprising:
a housing shaped and dimensioned for intralumenal deployment into and retention in a vagina of a human or animal subject;
a drug-dispensing portion which contains at least one drug and comprises a mechanical displacement element and an actuator, the drug-dispensing portion being configured to dispense the drug from the housing by causing the actuator to advance the mechanical displacement element through the housing;
a permeability enhancer-dispensing portion configured to release or generate a permeability enhancing substance to disrupt at least one region of a mucosal barrier of the vagina adjacent to the housing by inhibiting enzyme activity or rendering the mucosal barrier more permeable to the at least one drug at a selected time while intravaginally deployed and retained in the vagina of the human or animal subject; and
a control module contained in the housing, the control module controlling the release or generation of the permeability enhancing substance and the dispensing of the at least one drug by activation of the actuator and mechanical displacement element;
wherein the device is operable to dispense the drug from the housing to a region of the mucosal barrier disrupted by the permeability enhancing substance.

2. The device of claim 1, wherein the device is configured to generate the permeability enhancing substance in vivo.

3. The device of claim 1, wherein the permeability enhancer-dispensing portion comprises an electrochemical element.

4. The device of claim 1, wherein the permeability enhancing substance comprises hydrogen peroxide.

5. The device of claim 1, wherein the permeability enhancing substance is stored in a first repository and the drug is stored in a second repository separate from the permeability enhancing substance.

6. The device of claim 1, wherein the drug comprises a protein or peptide.

7. The device of claim 1, wherein the drug comprises a hormone or steroid.

8. The device of claim 1, further comprising a receiver adapted to receive power or control signals from a transmitting device when the device is deployed in the vagina.

9. The device of claim 1, wherein the control module is configured to sequence dispensing of the at least one drug from the drug-dispensing portion and release or generation of the permeability enhancing substance from the permeability-enhancer dispensing portion.

10. The device of claim 1, wherein the permeability enhancing substance comprises a chemical enhancer selected from the group consisting of DMSO, hydrogen peroxide, propylene glycol, oleic acid, cetyl alcohol, benzalkonium chloride, sodium lauryl sulphate, isopropyl myristate, Tween 80, dimethyl sulfoxide, dimethyl formamide, dimethyl acetamide, sodium lauroylsarcosinate, sorbitan monolaurate, methylsulfonylmethane, Azone, terpenes, phosphatidylcholine dependent phospholipase C, triacyl glycerol hydrolase, acid phosphatase, phospholipase A2, a concentrated saline solution, and a combination thereof.

11. The device of claim 1, wherein the permeability enhancing substance comprises an enzyme inhibitor selected from the group consisting of protease inhibitors, antiretrovirals, diisopropylfluorophosphate (DFP), α-difluoromethylornithine (DFMO), trypanothione reductase, methotrexate, allopurinol, acyclovir, and a combination thereof.

12. The device of claim 1, wherein the permeability enhancer-dispensing portion comprises a positive displacement element for actively dispensing the permeability enhancing substance from the housing selected from the group consisting of a mechanical displacement element, an osmotic swelling displacement element, a gas-volume displacement element, a magnetically-induced phase transformation element, a thermally-induced phase transformation element, a piezoelectric actuator, an electrostatically-induced compression element, an actuatable dispensing valve with a static pressure head and a combination thereof.

13. The intravaginal device of claim 1, wherein the mechanical displacement element comprises a piston.

14. A method for local transmucosal delivery of a drug to a human or animal subject comprising:
deploying and retaining a drug delivery device within a vagina of the human or animal subject, the device comprising a housing;
releasing from, or generating within, the device a permeability enhancing substance such that the permeability enhancing substance contacts and disrupts a region of the mucosal barrier of the vagina by inhibiting enzyme activity or rendering the mucosal barrier more permeable to the drug; and then after the mucosal barrier has been disrupted,
dispensing from the drug delivery device the drug by a positive displacement process such that the drug is delivered to the region of the mucosal barrier that has been disrupted by the permeability enhancing substance,
wherein the positive displacement process comprises driving a displacement element through a drug repository containing the drug to mechanically dispense the drug from the housing.

15. The method of claim 14, wherein the drug comprises a protein or peptide.

16. The method of claim 14, wherein the permeability enhancing substance comprises hydrogen peroxide.

17. The method of claim 14, wherein the permeability enhancing substance comprises a chemical enhancer selected from the group consisting of DMSO, propylene glycol, oleic acid, cetyl alcohol, benzalkonium chloride, sodium lauryl sulphate, isopropyl myristate, Tween 80, dimethyl sulfoxide, dimethyl formamide, dimethyl acetamide, sodium lauroyl-sarcosinate, sorbitan monolaurate, methylsulfonylmethane, Azone, terpenes, phosphatidylcholine dependent phospholipase C, triacyl glycerol hydrolase, acid phosphatase, phospholipase A2, a concentrated saline solution, and a combination thereof.

18. The method of claim 14, wherein the permeability enhancing substance comprises an enzyme inhibitor selected from the group consisting of protease inhibitors, antiretrovirals, diisopropylfluorophosphate (DFP), α-difluoromethylornithine (DFMO), trypanothione reductase, methotrexate, allopurinol, acyclovir, and a combination thereof.

19. The method of claim 14, wherein the displacement element comprises a piston.

20. An intravaginal device for transmucosal drug delivery comprising:
 a cylindrical housing configured for intravaginal deployment into and for holding the device in place in a vagina by frictional engagement between the housing and mucosal tissue of the vagina of a human or animal subject;
 a drug dispenser containing a drug, the drug dispenser having one or more nozzles and a positive displacement element adapted to dispense the drug from the housing through the one or more nozzles by positive displacement; and
 a permeability enhancer dispenser configured to release or generate a permeability enhancing substance to disrupt at least one region of a mucosal barrier adjacent to the housing by inhibiting enzyme activity or rendering the mucosal barrier more permeable to the drug at a selected time while deployed and retained in the vagina of the human or animal subject,
 wherein the device is operable to dispense the drug from the housing to the at least one region of the mucosal barrier disrupted by the permeability enhancing substance, and
 wherein the positive displacement element comprises a displacement element configured to be advanced through a drug repository containing the drug to mechanically dispense the drug from the housing.

21. The device of claim 20, wherein the permeability enhancer dispenser comprises one or more electrochemical elements configured to generate hydrogen peroxide in vivo.

22. The device of claim 20, further comprising a controller configured to control the actuation of the displacement element and the permeability enhancer dispenser.

23. The device of claim 20, wherein the drug comprises a protein or peptide.

24. The intravaginal device of claim 20, wherein the displacement element comprises a piston.

25. A medical device comprising:
 a housing configured for intralumenal deployment into and retention in a lumen of a human or animal subject;
 a permeability enhancer-dispensing portion comprising an array of electrochemical elements on an exterior of the housing, each electrochemical element being configured to generate hydrogen peroxide to disrupt at least one region of a mucosal barrier of the lumen adjacent to the housing at a selected time while intralumenally deployed in the human or animal subject; and
 a drug dispensing portion configured to dispense a drug from a drug repository disposed within the housing to the at least one region of the mucosal barrier disrupted by the hydrogen peroxide.

26. The medical device of claim 25, wherein the housing is cylindrical and configured for intravaginal deployment into and for holding the device in place in a vagina by frictional engagement between the housing and vaginal mucosal tissue of the human or animal subject.

* * * * *